(12) United States Patent
Lazar et al.

(10) Patent No.: US 9,603,604 B2
(45) Date of Patent: Mar. 28, 2017

(54) ORTHOPAEDIC CUTTING BLOCK

(71) Applicants: Scott C. Lazar, Cromwell, IN (US); Richard A. Lane, Fort Wayne, IN (US); Chris Bremer, Warsaw, IN (US)

(72) Inventors: Scott C. Lazar, Cromwell, IN (US); Richard A. Lane, Fort Wayne, IN (US); Chris Bremer, Warsaw, IN (US)

(73) Assignee: Symmetry Medical Manufacturing, Inc., Warsaw, IN (US)

( * ) Notice: Subject to any disclaimer, the term of this patent is extended or adjusted under 35 U.S.C. 154(b) by 915 days.

(21) Appl. No.: 13/660,019

(22) Filed: Oct. 25, 2012

(65) Prior Publication Data

US 2013/0296871 A1 Nov. 7, 2013

Related U.S. Application Data

(60) Provisional application No. 61/553,014, filed on Oct. 28, 2011.

(51) Int. Cl.
*A61F 5/00* (2006.01)
*A61B 17/15* (2006.01)

(52) U.S. Cl.
CPC ............ *A61B 17/15* (2013.01); *A61B 17/155* (2013.01)

(58) Field of Classification Search
CPC .................................................... A61B 17/15
USPC ........................................................ 606/87
See application file for complete search history.

(56) References Cited

U.S. PATENT DOCUMENTS

| | | | |
|---|---|---|---|
| 4,892,093 A | 1/1990 | Zarnowski et al. | |
| 4,926,847 A | 5/1990 | Luckman | |
| 5,749,876 A | 5/1998 | Duvillier et al. | |
| 5,766,259 A | 6/1998 | Sammarco | |
| 7,182,767 B2 | 2/2007 | Canonaco et al. | |
| 7,364,581 B2 | 4/2008 | Michalowicz | |
| 7,621,919 B2 | 11/2009 | Williams, III et al. | |
| 7,666,187 B2 | 2/2010 | Axelson, Jr. et al. | |
| 7,967,824 B2 | 6/2011 | Thau et al. | |
| 7,998,142 B2 | 8/2011 | Canonaco et al. | |
| 8,323,288 B2 | 12/2012 | Zajac | |
| 2005/0203531 A1 | 9/2005 | Lakin et al. | |
| 2005/0228393 A1 | 10/2005 | Williams, III et al. | |
| 2007/0055270 A1 | 3/2007 | Canonaco et al. | |
| 2007/0073306 A1* | 3/2007 | Lakin ................... | A61B 17/155 606/87 |
| 2007/0270872 A1 | 11/2007 | Thau et al. | |
| 2008/0195109 A1 | 8/2008 | Hunter et al. | |

(Continued)

OTHER PUBLICATIONS

European Search Report dated Jan. 10, 2013 for European Patent Application No. EP 12 19 0113 (5 pages).

*Primary Examiner* — David Isabella
*Assistant Examiner* — Christine Nelson
(74) *Attorney, Agent, or Firm* — Taylor IP, P.C.

(57) ABSTRACT

A bone cutting block includes: a plurality of saw slot plates each including a plurality of ends opposing one another, each of the plurality of ends including a locating feature, the plurality of saw slot plates defining at least one slot therebetween which is configured for receiving a bone saw blade therethrough to make a predefined cut in a bone; and two side plates opposing one another, including a plurality of locating features, and supporting the plurality of saw slot plates, each locating feature of the plurality of saw slot plates being connected with a respective one of the plurality of locating features of the side plates.

5 Claims, 6 Drawing Sheets

(56) References Cited

U.S. PATENT DOCUMENTS

| | | |
|---|---|---|
| 2009/0082774 A1 | 3/2009 | Oti et al. |
| 2009/0088762 A1 | 4/2009 | Koenenmann |
| 2010/0010493 A1 | 1/2010 | Dower |
| 2010/0185202 A1 | 7/2010 | Lester et al. |
| 2010/0191244 A1 | 7/2010 | White et al. |
| 2010/0268240 A1 | 10/2010 | McGinley et al. |
| 2011/0130762 A1 | 6/2011 | Metzger et al. |
| 2012/0143199 A1 | 6/2012 | Young |

* cited by examiner

ORTHOPAEDIC CUTTING BLOCK

CROSS REFERENCE TO RELATED APPLICATIONS

This is a non-provisional application based upon U.S. provisional patent application Ser. No. 61/553,014, entitled "ORTHOPAEDIC CUTTING BLOCK", filed Oct. 28, 2011, 2011, which is incorporated herein by reference.

BACKGROUND OF THE INVENTION

1. Field of the Invention

The present invention relates to orthopaedic devices, and, more particularly, to orthopaedic cutting blocks.

2. Description of the Related Art

Orthopaedic surgeons often attach implants to bones in an effort to improve the quality of life of a patient. Before the implant can be attached to the bone, the bone must often be prepared to receive the implant. Preparing the bone to receive the implant can involve cutting the bone precisely and accurately in one or more places. To make such cuts, a surgeon may use an orthopaedic cutting block, which can be variously referred to as a surgical cutting guide, a cutting guide, a bone cutting fixture, or a bone cutting block. When using such cutting guides, a surgeon may insert a bone saw blade through a slot formed by the cutting guide so that the bone saw blade cuts the bone at a precise angle and location. In this way portions of the bone can be resected.

For example, the surgeon often prepares the distal end of a femur to receive a femoral implant during total knee replacement surgery. This preparation involves making a transverse cut in the distal end of the femur and thereby resecting a portion of the femur. After resecting the femur in this manner, four additional cuts can be made using an orthopaedic cutting block, thereby resecting portions of the distal femur away from the remaining femur. These four cuts can be referred to as follows: the anterior cut; the posterior cut; the anterior chamfer cut; and the posterior chamfer cut. Such orthopaedic cutting blocks, however, can involve a high cost stemming at least in part from a large time expenditure, expensive manufacturing equipment, and high labor costs. Further, such cutting blocks can present problems as far as disposability. Further, such cutting blocks can be made of plastic. Durability and cost of such blocks can be problems. Cutting blocks can be made from a single metal block from which material is taken away (such as by machining) to form various slots in the block to make the four cuts.

What is needed in the art is a bone cutting block which is relatively inexpensive to manufacture.

SUMMARY OF THE INVENTION

The present invention provides a bone cutting block which includes side plates, a plurality of saw slot plates, and a chamfer plate, each of the plates being manufactured and connected together in a relatively inexpensive manner.

The invention in one form is directed to a bone cutting block which includes: a plurality of saw slot plates each including a plurality of ends opposing one another, each of the plurality of ends including a locating feature, the plurality of saw slot plates defining at least one slot therebetween which is configured for receiving a bone saw blade therethrough to make a predefined cut in a bone; and two side plates opposing one another, including a plurality of locating features, and supporting the plurality of saw slot plates, each locating feature of the plurality of saw slot plates being connected with a respective one of the plurality of locating features of the side plates.

The invention in another form is directed to a method of forming a bone cutting block, the method including the steps of: forming a plurality of saw slot plates and two side plates, the plurality of saw slot plates each including a plurality of ends opposing one another, each of the plurality of ends including a locating feature, the side plates including a plurality of locating features; supporting the plurality of saw slot plates using the side plates, each locating feature of the plurality of saw slot plates being connected with a respective one of the plurality of locating features of the side plates and the side plates thereby opposing one another, the plurality of saw slot plates defining at least one slot therebetween which is configured for receiving a bone saw blade therethrough to make a predefined cut in a bone.

The invention in yet another form is directed to a method of forming a bone cutting block, the method including the steps of: stamping a plurality of walls from at least one blank; connecting, after the step of stamping, the plurality of walls together, the plurality of walls defining at least one slot therebetween which is configured for receiving a bone saw blade therethrough to make a predefined cut in a bone.

An advantage of the present invention is that the cutting block can be inexpensive, lightweight, and innovative.

Yet another advantage is that the cutting block can be a single orthopaedic cutting block which can be used to perform four different cuts in a femur, the four cuts being an anterior cut, a posterior cut, an anterior chamfer cut, and a posterior chamfer cut in the distal end of a femur.

Yet another advantage is that the cutting block can be manufactured by stamping and thus provide large quantities and a low piece price. The cutting block can also be manufactured by sheet metal processing, wire EDM (that is, electric discharging machining), and/or full machining (such as milling and/or lathing).

Yet another advantage is that some of the components of the cutting block (such as the saw slot plates) can be used for numerous customer designs; that is, these plates can be common. On the other hand, other components of the cutting block (such as the side plates) can be made specific (that is, customized) for each customer. For example, the side plates can be customized by changing the size of the side plates. This common and custom feature of the present invention allows for cost savings in manufacturing that can be passed onto customers.

Yet another advantage is that the simplistic design of the cutting block allows for straightforward changes to adapt for a range of class sizes from small to large. For example, while no shape change is required, the size of the components can be changed so as to be smaller or larger. The components can be sized larger in height and width.

Yet another advantage is that the cutting block can be a disposable or reusable instrument. The cutting block can be made out of a medical grade stainless steel. Alternatively, the cutting block can be made out of other materials, such as ceramic, PEEK (that is, polyether ether ketone), carbon fiber, and plastic (glass filled).

Yet another advantage is that the components of the cutting block (that is, for example, the side plates, the saw slot plates, and the chamfer plate) can have the same thickness of material or can have, alternatively, various sizes.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention, and such exemplifications are not to be construed as limiting the scope of the invention in any manner.

DETAILED DESCRIPTION OF THE INVENTION

Figure 1:
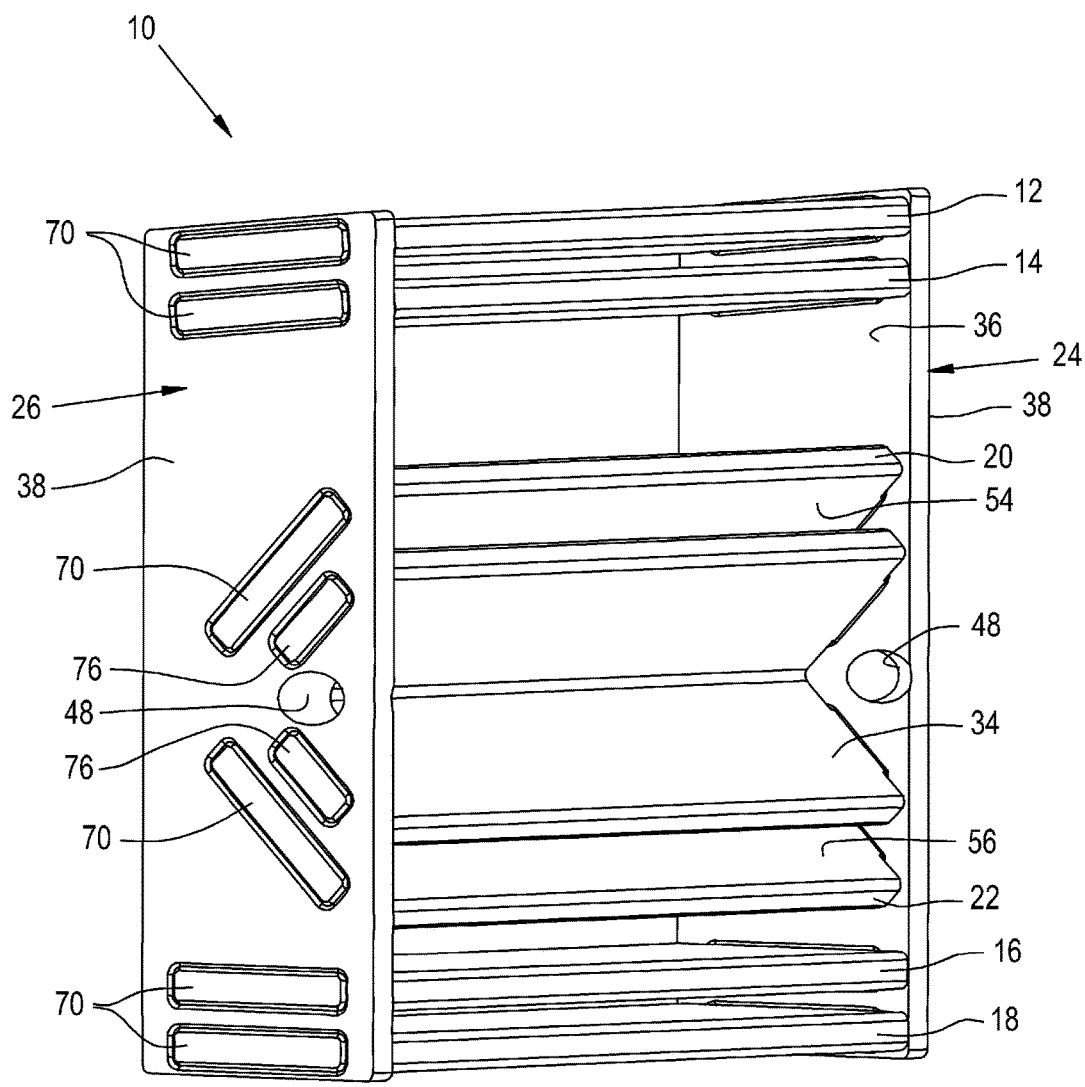
FIG. 1 is a perspective view of a bone cutting block according to the present invention.
Figure 2:
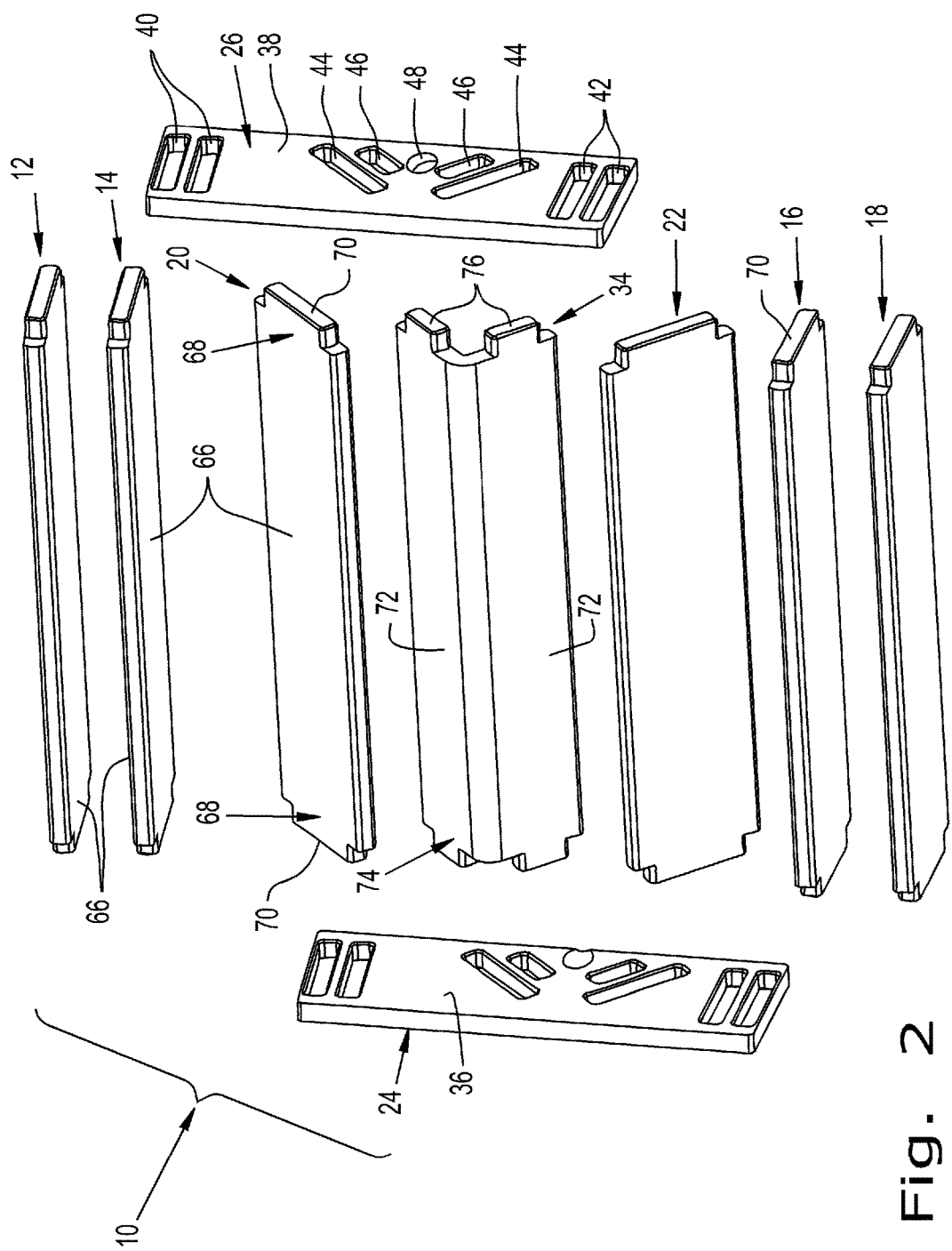
FIG. 2 is an exploded view of the bone cutting block of FIG. 1.
Figure 3:
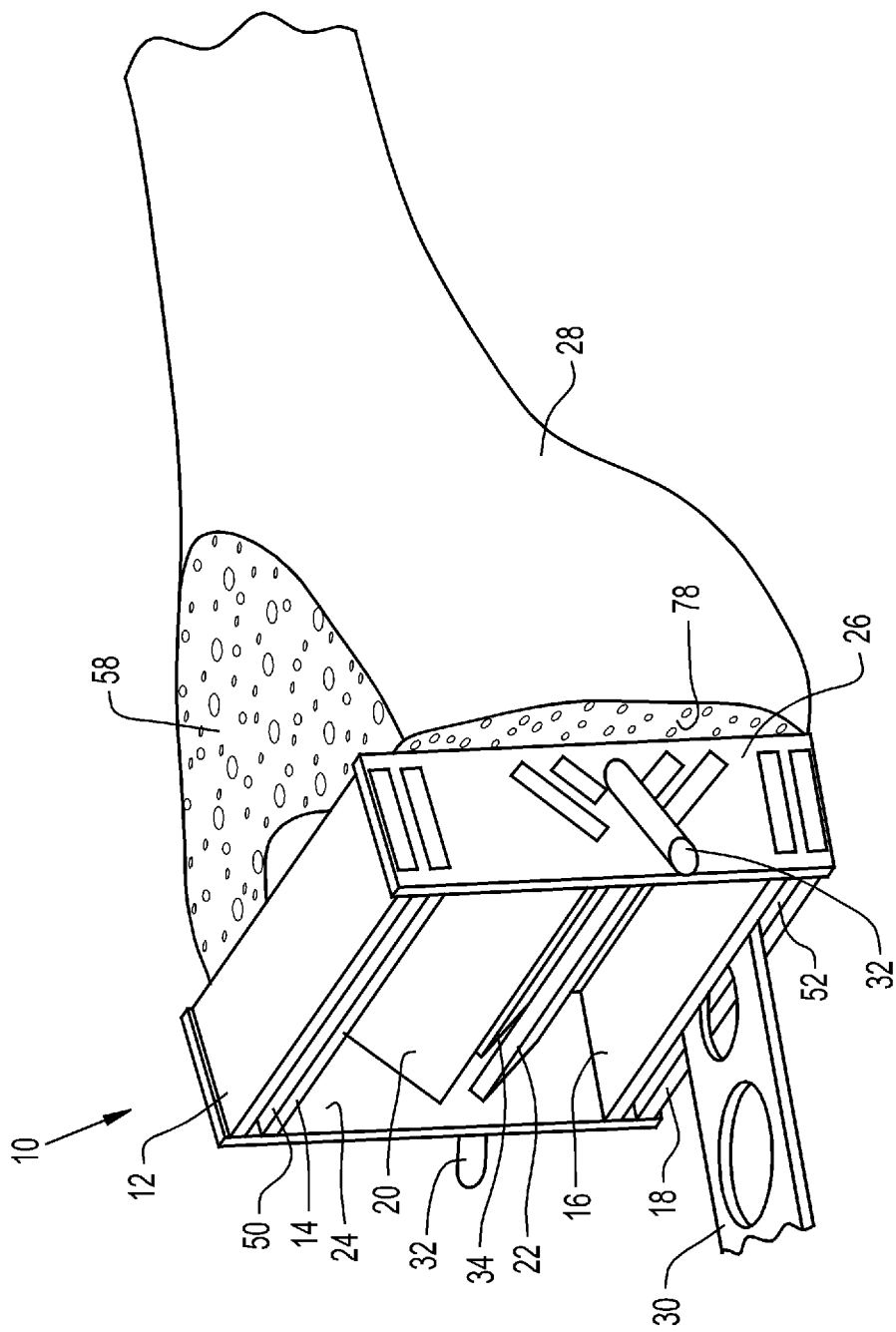
FIG. 3 is a perspective view of the bone cutting block of FIG. 1, the bone cutting block being positioned adjacent the distal end of a femur and a bone saw being shown in use with the bone cutting block.

Referring now to the drawings, and more particularly to FIGS. 1-4, there is shown a bone cutting block 10 (which can be variously referred to, as indicated above, as an orthopaedic cutting block, a bone cutting guide, a cutting guide, or a bone cutting fixture) which generally includes a plurality of saw slot plates 12, 14, 16, 18, 20, 22 and two opposing side plates 24, 26 (side plates 24, 26 oppose one another in their relative positioning). FIG. 3 shows that cutting block 10 is used when resecting a bone 28 (which can be a femur, for example) with a bone saw blade 30. In an exemplary embodiment of the present invention, the cutting block 10 can be used to resect the distal end of a femur 28. The cutting block 10 of the present invention, however, is not limited to resecting femurs 28 but can be used to resect other bones as well.

FIGS. 1-4 show that cutting block 10, according to one embodiment of the present invention, includes two side plates 24, 26, six saw slot plates 12, 14, 16, 18, 20, 22, and one chamfer plate 34. Each side plate 24, 26 can be formed substantially identical relative to one another and thus a description of one serves as a description of the other unless otherwise noted. Similarly, each saw slot plate 12, 14, 16, 18, 20, 22 can be formed substantially identical relative to one another and thus a description of one serves as a description of the other unless otherwise noted. The phrase "substantially identical" is used herein to account for manufacturing tolerances.

Side plates 24, 26 oppose one another with saw slot plates 12, 14, 16, 18, 20, 22 and chamfer plate 34 being positioned therebetween, side plates 24, 26 supporting saw slot plates 12, 14, 16, 18, 20, 22 and chamfer plate 34. Each side plate 24, 26 includes an inner surface 36 and an outer surface 38 opposing inner surface 36 of the respective side plate 24, 26, inner surface 36 facing saw slot plates 12, 14, 16, 18, 20, 22 and chamfer plate 34. Each side plate 24, 26 can be generally rectangular in shape (extending longitudinally) and can have a substantially constant thickness. Inner surface 36 can be substantially parallel to outer surface 38 of a respectively same side plate 24, 26. Each side plate 24, 26 includes a plurality of locating features 40, 42, 44, 46. Each locating feature 40, 42, 44, 46 of side plates 24, 26 can be a hole, such as a through-hole extending from inner surface 36 to outer surface 38 of a respective side plate 24, 26. Each of these holes 40, 42, 44, 46 can be referred to as a locating hole. FIGS. 1-4 show that each side plate 24, 26 includes two substantially parallel anterior locating holes 40, two substantially parallel posterior locating holes 40, two centrally located saw slot plate locating holes 44 that are angled relative to one another, two centrally located chamfer plate locating holes 46 that are angled relative to one another, and a single centrally located pin hole 48. Each pin hole 48 receives a respective pin 32, pin 32 being used to secure cutting block 10 to a transverse surface 78 of the distal femur 28 resulting from a transverse cut through the distal femur 28 and thereby a resection of the femur 28. Pin 32 thus serves to align and/or attach cutting block 10 to femur 28. Pin 32 can otherwise be a screw which screws into bone 28; for simplicity herein, generally only pin 32 is referenced in the description but it is understood that a screw could be used in place of a pin.

A plurality of saw slot plates 12, 14, 16, 18, 20, 22 define at least one slot 50, 52, 54, 56 therebetween which is configured for receiving bone saw blade 30 therethrough to make a predefined cut 58, 60, 62, 64 in bone 28. FIG. 2 shows that each saw slot plate 12, 14, 16, 18, 20, 22 can have two substantially planar sides 66 which run substantially parallel to one another. Further, each saw slot plate 12, 14, 16, 18, 20, 22 includes a plurality of ends 68 which oppose one another. Each end 68 of saw slot plate 12, 14, 16, 18, 20, 22 includes a locating feature 70. Each locating feature 70 of saw slot plates 12, 14, 16, 18, 20, 22 is an outwardly facing projection 70 (which can also be referred to as a boss). Each locating feature 70 of saw slot plates 12, 14, 16, 18, 20, 22 are connected (attached) with a respective one of the plurality of locating features 40, 42, 44 of side plates 24, 26. Thus, each projection 70 of saw slot plates 12, 14, 16, 18, 20, 22 is inserted in and fits within a respective locating hole 40, 42, 44 of a respective side plate 24, 26.

Chamfer plate 34 includes two planar sections 72 which are joined together. Chamfer plate 34 includes a plurality of opposing ends 74 (ends 74 oppose one another), each end 74 including at least one locating feature 76 formed as an outwardly facing projection. Each outwardly facing projection 76 of chamfer plate 34 connects with (attaches to) a respective one of the locating features 40, 42, 44, and 46 (in particular, locating feature 46) of side plates 24, 26. FIG. 2 shows that each planar section 72 includes a projection 76 such that each chamfer plate 34 includes four such projections 76.

Figure 4:
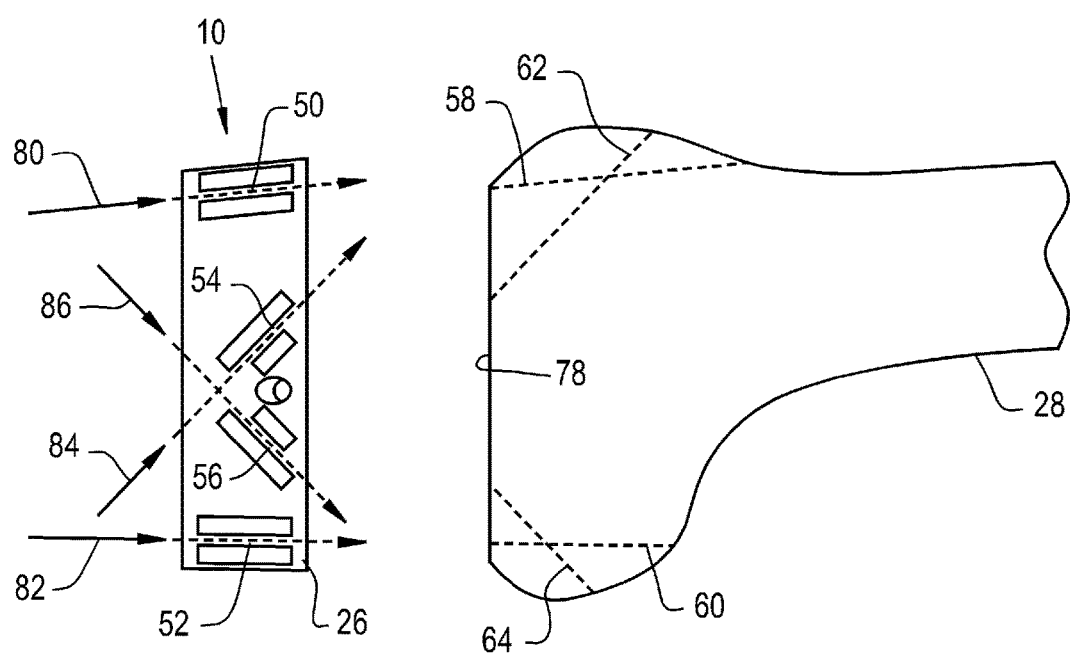
FIG. 4 is a side view of the bone cutting block of FIG. 1, the bone cutting block being spaced apart from but near the distal end of a femur which has been cut transversely.
Figure 5:
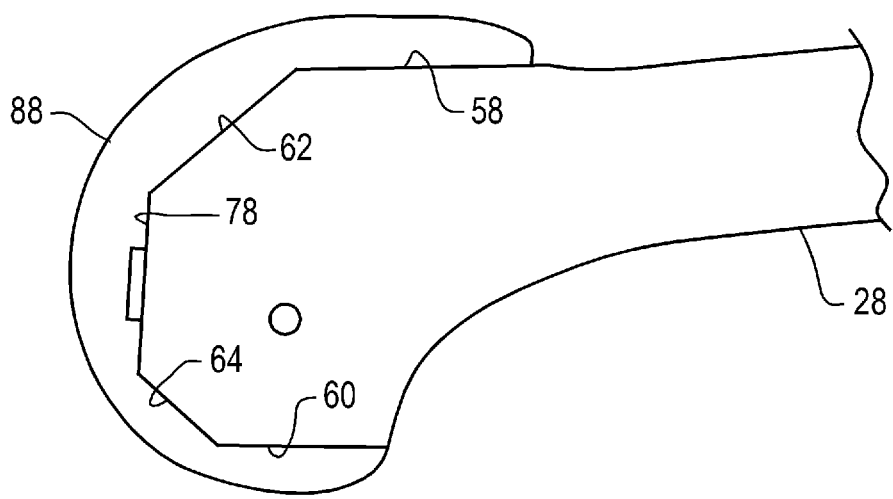
FIG. 5 is shows a schematic side view of a femur with an implant mounted on the femur after the femur has been resected using the bone cutting block of FIG. 1.

The plurality of saw slot plates 12, 14, 16, 18, 20, 22 includes a first saw slot plate 12, a second saw slot plate 14, a third saw slot plate 16, a fourth saw slot plate 18, a fifth saw slot plate 20, and a sixth saw slot plate 22. The at least one slot 50, 52, 54, 56 includes a first slot 50, a second slot 52, a third slot 54, and a fourth slot 56. First saw slot plate 12 and second saw slot plate 14 together form first slot 50 which is configured for receiving bone saw blade 30 to make an anterior cut 58 in bone 28; bone 28 can be a femur 28 of a human being, as shown in FIGS. 3-5. Third saw slot plate 16 and fourth saw slot plate 18 together form second slot 52 which is configured for receiving bone saw blade 30 to make a posterior cut 60 in femur 28. Fifth saw slot plate 20 and one planar section 72 of chamfer plate 34 together form third slot 54 which is configured for receiving bone saw blade 30 to make an anterior chamfer cut 62 in femur 28. Sixth saw slot plate 22 and another planar section 72 of chamfer plate 34 together form fourth slot 56 which is configured for receiving bone saw blade 30 to make a posterior chamfer cut 64 in femur 28. Each of the saw slot plates 12, 14, 16, 18, 20, 22, side plates 24, 26, and chamfer plate 34 can be solid or, alternatively, hollow. Side plates 24, 26 do not have columns or poles mounted inside them to support them. Transverse cross-sections of each of the saw slot plates 12, 14, 16, 18, 20, 22, side plates 24, 26, and planar sections 72 of the chamfer plate 34 can be rectangular.

Arrow 80 in FIG. 4 shows the direction which bone saw 30 travels through first slot 50, and broken line 58 in FIG. 4 generally shows anterior cut 58 that would be formed in femur 28 as bone saw blade 30 follows arrow 80 through femur 28. Arrow 82 in FIG. 4 shows the direction which bone saw blade 30 travels through second slot 52, and broken line 60 in FIG. 4 generally shows posterior cut 60 that would be formed in femur 28 as bone saw blade 30 follows arrow 82 through femur 28. Arrow 84 in FIG. 4 shows the direction which bone saw blade 30 travels through third slot 54, and broken line 62 in FIG. 4 generally shows anterior chamfer cut 62 that would be formed in femur 28 as bone saw blade 30 follows arrow 84 through femur 28. Arrow 86 in FIG. 4 shows the direction which bone saw blade 30 travels through fourth slot 56, and broken line 64 in FIG. 4 generally shows anterior cut 64 that would be formed in femur 28 as bone saw blade 30 follows arrow 86 through femur 28. Bone saw blade 30 can be inserted in any of slots 50, 52, 54, and 56 to cut the distal femur 28 and thereby form the respective cut 58, 60, 62, 64. FIG. 4 also shows schematically the distal end of femur 28 with a transverse cut already made in the distal end of femur 28 to form transverse surface 78 upon which cutting block 10 of the present invention is positioned. Transverse surface 78 in the distal end of femur 28 can be formed by using something other than cutting block 10 of the present invention; it is contemplated that a first block would be used by a surgeon to cut the transverse cut in the distal end of femur 28 to form transverse surface 78, and then cutting block 10 of the present invention would be used to cut the four remaining cuts in the distal end of femur 28 (the four remaining cuts being anterior cut 58, posterior cut 60, anterior chamfer cut 62, and posterior chamfer cut 64).

FIG. 5 shows the distal end of femur 28 which has been prepared to receive implant 88. The distal end of femur 28 has the transverse surface 78 which has been cut into femur 28. Further, the distal end of femur 28 has anterior cut 58, posterior cut 60, anterior chamfer cut 62, and posterior chamfer cut 64. Further, implant 88 is mounted to the distal end of femur 28. The distal end of femur 28 can be formed with cuts 58, 60, 62, and 64 from any of the embodiments of the cutting block of the present invention which are disclosed herein (although the relative dimensions of the cuts relative to one another may be different).

Cutting block 10 can be formed by stamping each component of cutting block 10 (a stamping operation can include removal of material). More specifically, each side plate 24, 26, each saw slot plate 12, 14, 16, 18, 20, 22, and chamfer plate 34 can be formed by stamping sheet metal. The sheet metal can be, for example, stainless steel, such as medical grade stainless steel. Side plates 24, 26, including each of the holes 40, 42, 44, 46, 48 in side plates 24, 26, can be stamped from a sheet metal blank. A two-step stamping process can be used to form holes 40, 42, 44, 46, 48 in each side plate 24, 26. For example, a first stamping step can stamp out a respective side plate 24, 26 circumference and each of holes 40, 42, 44, 46 except for pin hole 48. A second stamping step can be used to stamp out pin hole 48, which is formed at an angle to the surfaces 36, 38 of side plate 24, 26. Pin holes 48 can alternatively be machined, such as by milling. Each of saw slot plates 12, 14, 16, 18, 20, 22 can also be stamped in a single stamping step or in multiple stamping steps; for example, a rectangular piece could be stamped and then the four corners of the rectangular piece could be stamped out to form the respective saw slot plate 12, 14, 16, 18, 20, 22. Further, chamfer plate 34 can be stamped out of sheet metal (in one or more stamping steps) and then bent to take its shape as shown in the figures.

Various options exist in being able to form cutting block 10. For example, the components of cutting block 10 can be made out of plastic, such as a hard plastic, which can be formed by molding or stamping, for example. Alternatively, the components of cutting block 10 can be stamped, formed (which includes a folding or bending operation), made by laser cutting, made using a water jet, made using a wire, made by typical machining (for example, mill, lathe, CNC (Computer Numerical Control), wire EDM (electrical discharge machining)), and/or made by Rapid Metal-laser sintering and/or direct metal laser sintering (DMLS).

After forming the individual components (side plates 24, 26, saw slot plates 12, 14, 16, 18, 20, 22, and chamfer plate 34), cutting block 10 can be assembled. The bosses 76 of one end 74 of chamfer plate 34 can be inserted in chamfer plate locating holes 46 in the first side plate 24 or 26 (either side plate 24, 26 can be the first side plate 24 or 26, and the other side plate 24, 26 can be the second side plate 24 or 26). The bosses 70 of the two saw slot plates 20, 22 closest to chamfer plate 34 can then be inserted into the saw slot plate chamfer locating holes 44 in the first side plate 24 or 26. The bosses 70 of the two saw slot plates 12, 14 forming anterior cut slot 50 can then be inserted into locating holes 40 in the first side plate 24 or 26. The bosses 70 of the two saw slot plates 16, 18 forming posterior cut slot 42 can then be inserted into locating holes 42 in the first side plate 24 or 26. The other side plate 24 or 26 can then be placed in a similar manner onto the components (saw slot plates 12, 14, 16, 18, 20, 22 and chamfer plate 34) already assembled. Saw slot plates 12, 14, 16, 18, 20, 22 and chamfer plate 34 can then be firmly attached to side plates 24, 26 by way of, for example, staking, welding, and/or laser welding the plates together. More specifically, the bosses 70, 76 can be staked or welded (such as laser welding or TIG (tungsten inert gas) welding) to the corresponding holes 40, 42, 44, 46 in side plates 24, 26. An appropriate filler can be used at the connection between the bosses 70, 76 and side plates 24, 26 and then polished, any seams or cracks thereby being removed for sterilization purposes and thus rendering cutting block 10 to be reusable. If staking is used, the bosses 70, 76 can be slip fit into the corresponding holes 40, 42, 44, 46 on side plates 24, 26, and then bosses 70, 76 can be compressed to cause an interference fit with the respective holes 40, 42, 44, 46 in side plates 24, 26. If cutting block 10 is to be disposable (i.e., a one-time use), the staking may be the preferred method of attachment. Cutting block 10, and/or the components (saw slot plates 12, 14, 16, 18, 20, 22, chamfer plate 34, and side plates 24, 26, and pins/screws 32) thereof, can be passivated at the appropriate time(s) during the manufacture of cutting block 10. According to one method, the holes in the side plates 24, 26 can be added during assembly of the plates of cutting block 10. The finish of the plates of cutting block 10 can be, for example, satin and have a 63 Ra (63/M) surface finish. The material can be, for example, 17-4 stainless steel of any of the plates of cutting block 10, and any of the plates can be heat treated at H900. The plates of cutting block 10 can be made in various sizes. Cutting block 10 can be polished, filled, and formed with rounded corners.

Alternatively, the individual components of cutting block 10 (saw slot plates 12, 14, 16, 18, 20, 22, side plates 24, 26, chamfer plate 34) can be assembled together manually, via an automated process (i.e., using robotics), and/or using an assembly fixture. In this way, the components of cutting block 10 can be positioned in predetermined locations relative to one another and then secured together. With an assembly fixture, the components of cutting block 10 can be positioned in a gage fixture and can be spaced apart, using gage shims (graphite or steel), at predetermined locations to maintain the saw slots while furnace brazing to secure the plates together. According to one embodiment of the present invention, the component parts of cutting block 10 can be secured together using furnace brazing (for example, laser, TIG (tungsten inert gas) welding, and fuse). For instance, projection 70 of a respective saw slot plate can be laser welded to a respective locating hole 40, 42, 44, 46 of a side plate 24, 26 and filled.

In use, after the transverse cut is made in the distal end of femur 28 to form transverse surface 78, the surgeon can mount cutting block 10 of the present invention to transverse surface 78. Cutting block 10 is mounted such that the rear of cutting block 10 abuts transverse surface 78 of femur 28, and the front of cutting block 10 faces the surgeon and away from transverse surface 78 of femur 28. Optionally, the cutting block could incorporate a center hole so that the intramedullary canal of the femur could be used to center the guide (a hole being drilled into the intramedullary canal to receive an alignment pin, for example). Two holes can be drilled into transverse surface 78 of the distal end of femur 28, these holes being used to receive alignment/mounting pins 32. After drilling these holes into femur 28, the rear of cutting block 10 can be positioned adjacent transverse surface 78, and alignment pins 32 or screws 32 can be inserted through pin holes 48 and into the holes drilled into transverse surface 78. If pins 32 are used, pins 32 can be pressed into the bone holes to form an interference fit therewith; if screws 32 are used, screws 32 can be screwed to bone 28. Pin holes 48 in side plates 24, 26 are smooth (not threaded). While not shown in FIG. 3, pins 32 or screws 32 can include a sufficiently sized head so that cutting block 10 does not slide away from transverse surface 78 along pins 32 or screws 32 but rather is pulled against femur 28 by way of the head. Absent a sufficiently sized head, the surgeon can hold (i.e., with the surgeon's fingers) cutting block 10 against transverse surface 78 while pins 32 keep cutting block 10 aligned. FIG. 3 specifically shows cutting block 10 of FIG. 1 in use. FIG. 3 shows cutting block 10 mounted to transverse surface 78 which has already been cut into the distal end of femur 28. Further, two pins 32 are used to secure cutting block 10 to transverse surface 78. Each pin 32 is mounted to transverse surface 78 of femur 28 (transverse surface 78 having been prepared by drilling two holes to receive pins 32) after traveling through pin holes 48 in side plates 24, 26 of cutting block 10. Because of the angle of pin holes 48, pins 32 can be held at an acute angle relative to side plates 24, 26 as pins 32 point generally back towards the front of cutting block 10. Each pin 32 can have a generally flat portion (the free end, which is not in contact with femur 28) for gripping with fingers, the flat portion abutting a cylindrical portion of pin 32; as indicated, in one embodiment of the present invention, cutting block 10 can be held against transverse surface 78 by the fingers of the surgeon. Cutting block 10 of the present invention has slots 50, 52, 54, 56 for making anterior cut 58, posterior cut 60, anterior chamfer cut 62, and posterior chamfer cut 64 in the distal end of femur 28. FIG. 3 shows bone saw blade 30 (which can be an electrically powered, reciprocating saw blade) inserted in slot 52 formed by the bottom two saw slot plates 16, 18. In this position, saw blade 30 forms posterior cut 60. FIG. 3 also shows that anterior cut 58 has already been formed in the distal end of femur 28. Depending upon the surgeon's preference, the order of the cuts can be as follows (this is provided by way of example, not by way of limitation): anterior cut 58; posterior cut 60; anterior chamfer cut 62; and then posterior chamfer cut 64. Thus, anterior cut slot 40 can receive bone saw blade 30 to make anterior cut 58. Posterior cut slot 52 can receive bone saw blade 30 to make posterior cut 60. Anterior chamfer cut slot 54 can receive bone saw blade 30 to make anterior chamfer cut 62. Posterior chamfer cut slot 56 can receive bone saw blade 30 to make posterior chamfer cut 64.

Figure 6:
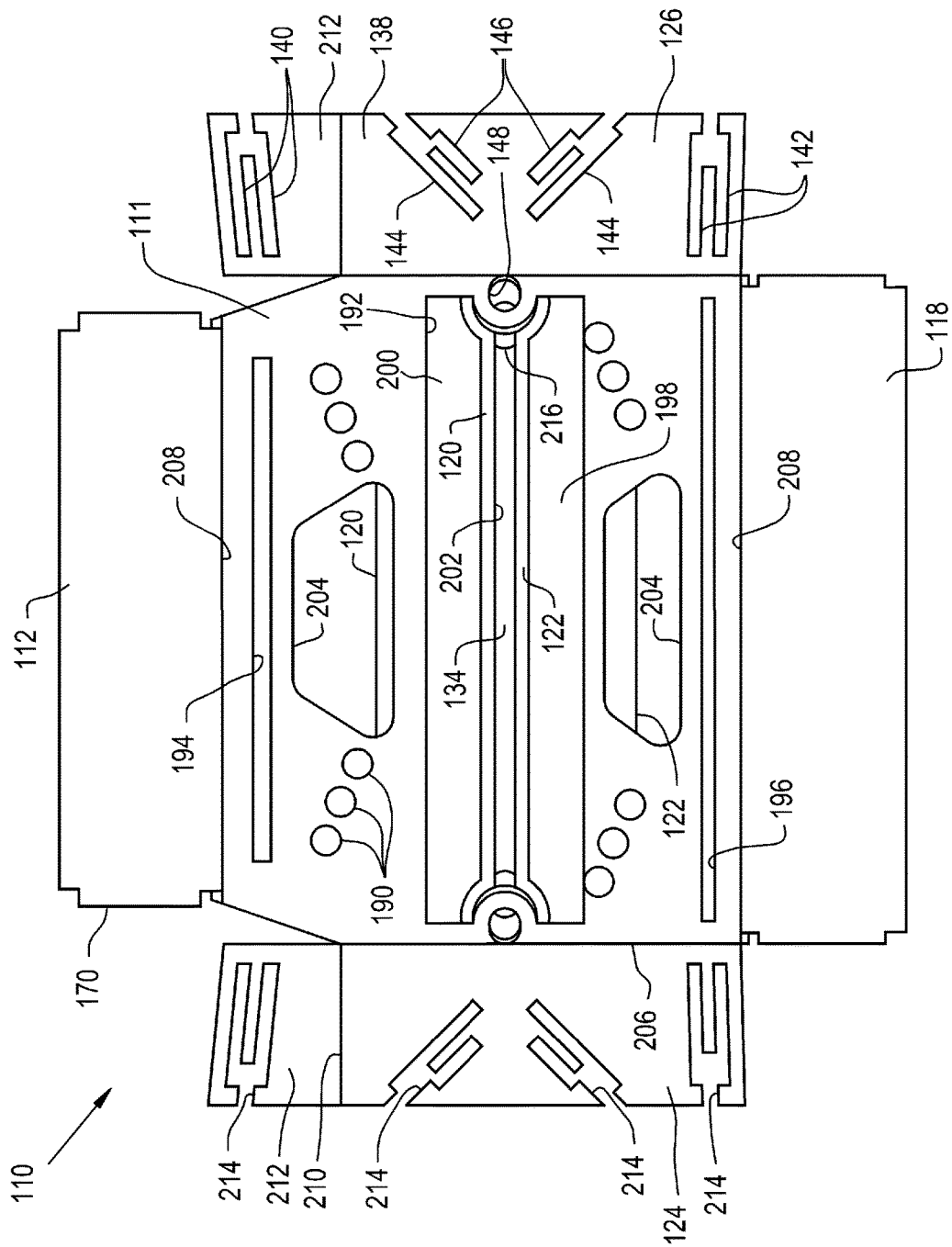
FIG. 6 is a front view of a partially formed bone cutting block according to another embodiment of the bone cutting block of the present invention the present invention.

FIG. 6 shows another embodiment of the cutting block according to the present invention. The cutting block of this embodiment is labeled as 110, and reference characters corresponding to parts of cutting block 10 are raised by 100. Cutting block 110 shown in FIG. 6 is a minimally invasive styled cutting block. FIG. 6 shows that cutting block 110 is not yet fully formed. Cutting block 110 includes a base plate 111, two side plates 124, 126, six saw slot plates (only saw slot plates 112, 118, 120, 122 are shown in FIG. 6), and a chamfer plate 134. Base plate 111 forms a face (more specifically, a face plate) which the surgeon views during the medical procedure, the opposing side of cutting block 110 being positioned against the transverse surface 78 formed after making the transverse cut in the distal end of the femur 28. Base plate 111 includes an anterior cut slot 194, a posterior cut slot 196, centrally located pin holes 148, additional pin holes 190 positioned in the anterior and posterior regions of base plate 111, and a transverse window 192. Anterior cut slot 194 of base plate 111 forms a slot through which bone saw blade 30 can pass, blade 30 then passing through the anterior cut slot formed between two saw slot plates (one being saw slot plate 112), and then to femur 28. Posterior cut slot 196 of base plate 111 forms a slot through which bone saw blade 30 can pass, blade 30 then passing through the posterior cut slot formed between two saw slot plates (one being saw slot plate 118), and then to femur 28. Centrally located pin holes 148 receive a pin or screw therethrough, the pin or screw mounting to femur 28; pin holes 148 can also align with aligned holes 216 in chamfer plate 134 before mounting to femur 28. The additional pin holes 190 can also be used for attachment and/or alignment to femur 28. The transverse window 192 includes inwardly projecting planar slants 198, 200 which generally converge toward one another but form a gap 202 therebetween, one slant (the lower slant in FIG. 6) being an anterior chamfer slant 198, the other slant (the upper slant in FIG. 6) being a posterior chamfer slant 200. The lower slant 198 forms a sliding wall leading to an aligned upper planar section of chamfer plate 134, the lower slant 200 and the upper planar section of chamfer plate 134 together forming a sliding surface for bone saw blade 30 to form an anterior chamfer cut 62. The upper slant 200 forms a sliding wall leading to an aligned lower planar section of chamfer plate 134, the upper slant 200 and the lower planar section of chamfer plate 134 together forming a sliding surface for bone saw blade 30 to form a posterior chamfer cut 64. Base plate 111 further includes anterior and posterior viewing windows 204 so that the surgeon can see through base plate to femur 28.

Side plates 124, 126 are similar to side plates 24, 26. Side plates 124, 126 are attached to opposing edges of base plate along fold lines 206; stated another way, base plate 111 is connected to side plates 124, 126 by way of a plurality of folds formed along fold lines 208 (thus, these plurality of folds are formed when side plates 124, 126 are folded or bent into the page of FIG. 6 (that is, away from the viewer of FIG. 6) along fold lines 208, side plates 124, 126 being substantially at right angles to the plane of base plate 111 after such folding of side plates 124, 126 along fold lines 208). Side plates 124, 126 include locating holes 142, 144, 146 for receiving projections 170 of saw slot plates 118, 120, 122 (as well as the saw slot plate corresponding to saw slot plate 16 but which is not shown in FIG. 6) and chamfer plate 134 as described relative to FIGS. 1-4. However, attached to one respective edge of side plates 124, 126 and along respective fold lines 210 are angle plates 212. Each angle plate 212 can be smaller than the side plates 124, 126 and have a square-ish shape. Each angle plate 212 includes locating holes 140 for holding saw slot plates (112, and the saw slot plate corresponding to saw slot plate 14 but which is not shown in FIG. 6) used to make the anterior cut 58. Side plates 124, 126 and angle plates 212 each include reliefs 214 (openings/gaps) along the edge of the respective plate. Each relief 214 serves to allow the saw blade 30 to swing out farther within the respective saw blade slot relative to side plates 124, 126 and angle plates 212. Optionally, depending upon the design of the reliefs 214, the reliefs 214 could be used to slide the respective saw slot plate into a respective locating hole 140, 142, 144, 146.

Each of the saw slot plates of cutting block 110 can be similar to the saw slot plates 12, 14, 16, 18, 20, 22 of cutting block 10. The six saw slot plates of cutting block 110 are used essentially in the same way as those of cutting block 10. FIG. 6 shows saw slot plates 112, 118, 120, 122 but omits showing the saw slot plates corresponding to saw slot plates 14 and 16; however, it is understood that cutting block 110 would have saw slot plates corresponding to saw slot plates 14 and 16. Two saw slot plates 112 and 118 of cutting block 110 are attached to base plate 111 along fold lines 208, as shown in FIG. 6. Further, as indicated in FIG. 6, the saw slot plates for anterior cut 58 can be of a different length relative to each other and relative to the other saw slot plates, given the angular relationship of angle plates 212 attached to side plates 124, 126. A portion of the saw slot plates 120, 122 for forming anterior chamfer cut 62 and posterior chamfer cut 64 are shown through the upper and lower (that is, the anterior and posterior region) windows 204 in FIG. 6. None of the saw slot plates of cutting block 110 are shown attached to side plates 124 or angle plates 212 in FIG. 6. However, it is understood that they would be so attached. Each of the saw slot plates of cutting block 110 has projections like those of the saw slot plates of FIG. 1. Optionally, each saw slot plate 120, 122 can include holes on each lateral end (near side plates 124, 126), these holes aligning with centrally located pin holes 148 in base plate 111 so as to accommodate an affixation and/or alignment pin or screw.

Chamfer plate 134 can be substantially similar to chamfer plate 34 of cutting block 10 (but can have the pin/screw holes 216 as described above). Thus, the outer surface of each of the planar sections of the chamfer plate 134 serve as sliding surfaces for bone saw blade 30 and work together with slants 198, 200 to guide the blade 30. Chamfer plate 134 also includes projections like chamfer plate 34.

Side plates 124, 126, angle plates 212, and the two saw slot plates 112, 118 all attached to base plate 111 can be folded along their respective fold lines 206, 208, 210 away from the viewer of FIG. 6 so that each of these plates can attach respectively to one another. In so doing, side plates 124, 126 and angle plates 212 are folded inwardly (away from the viewer of FIG. 6). In this way, locating features 170 from each of the saw slot plates and the chamfer plate 134 can be attached to corresponding locating holes 140, 142, 144, 146 of side plates 124, 126 and angle plates 112. Thus, the top saw slot plate 112 forming anterior cut slot 50 is attached to top locating holes 140 in angle plates 212. The bottom saw slot plate (not shown in FIG. 6) forming anterior cut slot 50 is attached to bottom locating holes 140 in angle plates 212. Further, the bottom saw slot plate 118 forming posterior cut slot 52 is attached to bottom locating holes 142 in side plates 124, 126. The top saw slot plate (not shown in FIG. 6) forming posterior cut slot 52 is attached to the top locating holes 142 for the posterior cut slot 152. Further, locating holes 144 of side plates 124, 126 receive corresponding projections (not shown in FIG. 6) from saw slot plates 120, 122, and locating holes 146 of side plates 124, 126 receive corresponding projections (not shown in FIG. 6) from chamfer plate 134. In an alternative embodiment, angle plates can be attached by way of a fold line to base plate 111, rather than to side plates 124, 126 by a fold line.

The structures shown in FIG. 6 can be stamped out of a metal or plastic. The relief lines 206, 208, 210 can be formed as shown in FIG. 6 and can serve as fold lines, the fold lines 206, 208, 210 being formed between the base plate 111 and each side plate 124, 126, between the base plate 111 and the top anterior cut saw slot plate 112, between the base plate 111 and the bottom posterior cut saw slot plate 118, and between each angle plate 212 and the respective side plate 124, 126. The structures shown in FIG. 6, including the shaping and the holes therein, can be formed by stamping and/or pressing. The fold lines 206, 208, 210 can be placed on the structure in any known manner, such as by using a press or machining. During assembly, the respective plates 112, 118, 124, 126, 212 can be folded along the fold lines 206, 208, 210. The side plates 124, 126 and the angle plates 212 can be folded and the top and bottom saw slot plates 112, 118 can be folded (away from the viewer of the page of FIG. 6) to form a box-like structure. One of the side plates 124, 126 and angle plates 212 can first receive the respective bosses (the projections 170) of the saw slot plates, and then the other side plate 124, 126 and angle plate 212 can receive the respective bosses 170 of the saw slot plates. Further, the attachments can be made secure by way of an interference fit, or by way of welding, or by way of staking, for example. While not shown, a rear face plate (adjacent transverse surface 78) can be attached to the structures (any or all of the side plates, angle plates, saw slot plates, and chamfer plate) in FIG. 6; the rear face plate can be part of the structure shown in FIG. 6 or can be a separate structure that is attached to the structure shown in FIG. 6. This way, the interior components of the cutting block 110 would be virtually fully enclosed. It is noted that the cutting block 110 of the present invention can be formed out of metal or a plastic, such as a hard plastic as mentioned herein. Thus, the present invention also provides a flat sheet metal process for making the cutting block 110.

In summary, the method of manufacture thus described relative to FIG. 6 is a formed manufacturing method. According to this manufacturing method, the side plates 124, 126 and the angle plates 212 can be attached to the base plate 111 as one piece and folded to form a part of the cutting block 110. If the side plates 124, 126 and the angle plates 212 are attached to the base plate 111, the base plate 111, the side plates 124, 126, and the angle plates 212 can be formed from the same metallic blank and stamped therefrom as one piece. The locating holes 140, 142, 144, 146 for all six of the saw slot plates and the chamfer plate 134 respectively on the side plates 124, 126 and the angle plates 212 can be stamped into this piece as well; the holes 140 in the angle plates 212 can optionally be formed in an additional stamping step given the angle of the holes 140 in the angle plates 212. The stamped piece (including the base plate 111, the side plates 124, 126, saw slot plates 112, 118, 120, 122, and the angle plates 112) can have reliefs formed thereon to form fold lines 206, 208, 210. The fold lines 206, 208, 210 thus delineate the side plates 124, 126, the angle plates 212, and saw slot plates 112, 118, and the base plate 111 from each other. The side plates 124, 126 and the angle plates 212 can then be folded (bent) so as to be substantially perpendicular relative to the base plate 111. Saw slot plates 112, 118 and the chamfer plate 134 can be inserted into the corresponding holes 140, 142, 144, 146 on the side plates 124, 126 and the angle plates 212 and staked and/or welded thereto, for example, first to one side plate/angle plate (124, 126, 212), and then to the other side plate/angle plate (124, 126, 212); the attachment of the saw slot plates to the side and angle plates (124, 126, 212) can be made selectively before or after folding a respective said plate/angle plate (124, 126, 212). The side plates 124, 126 can have tabs (not shown) which are stamped and bent outwardly from the side plates 124, 126, the tabs having a pin hole therein to accommodate a pin or screw. Thus, side plates 124, 126, saw slot plates 112, 118, and angle plates 212 can be folded relative to base plate 111 to form a shell. The plates can be stamped and/or machined, the holes (such as the locating holes in the side plates) therein also being stamped, machined, and/or drilled. Thus, each plate can be created in the flat (from one or more blanks, such as a metal blank), the blank being punched out to form the plates, certain ones of the plates then being folded as described above. The plates can be laser welded together at their edges or otherwise at their connecting points and filled.

The cutting block 110 of FIG. 6 can be made differently. For example, each angle plate 212 can be attached to the base plate 111 rather than to the side plates 124, 126. Each angle plate 212 could still fold into the plane of the page to form the box-like structure of the cutting block 110.

Further, the cutting block 110 of FIG. 6 could be made according to a sheet metal manufacturing method. According to this method, the base plate 111, the side plates 124, 126, the angle plates 212, the saw slot plates (all six), and the chamfer plate 134 can be stamped as separate pieces and then attached to one another. The attachment between the base plate 111 and the side plates/angle plates (124, 126, 212) can be by way of a snap-fit arrangement, welding, or staking, for example.

The present invention further provides a method of forming bone cutting block 10, 110. The method includes the steps of: forming a plurality of saw slot plates 12, 14, 16, 18, 20, 22, 112, 118, 120, 122 and two side plates 24, 26, 124, 126 the plurality of saw slot plates 12, 14, 16, 18, 20, 22, 112, 118, 120, 122 each including a plurality of ends 68 opposing one another, each of the plurality of ends 68 including a locating feature 70, 170, side plates 24, 26, 124, 126 including a plurality of locating features 40, 42, 44, 46, 140, 142, 144, 146; supporting the plurality of saw slot plates 12, 14, 16, 18, 20, 22, 112, 118, 120, 122 using side plates 24, 26, 124, 126 each locating feature 70, 170 of the plurality of saw slot plates 12, 14, 16, 18, 20, 22, 112, 118, 120, 122 being connected with a respective one of the plurality of locating features 40, 42, 44, 140, 142, 144 of side plates 24, 26, 124, 126 and side plates 24, 26, 124, 126 thereby opposing one another, the plurality of saw slot plates 12, 14, 16, 18, 20, 22, 112, 118, 120, 122 defining at least one slot 50, 52, 54, 56 therebetween which is configured for receiving bone saw blade 30 therethrough to make a predefined cut 58, 60, 62, 64 in bone 28. Each locating feature 70, 170 of the plurality of saw slot plates 12, 14, 16, 18, 20, 22, 112, 118, 120, 122 can be an outwardly facing projection 70, 170 each side plate 24, 26 including an inner surface 36 and an opposing outer surface 38, 138 inner surface 36 facing the plurality of saw slot plates 12, 14, 16, 18, 20, 22, 112, 118, 120, 122 each of the plurality of locating features 40, 42, 44, 46, 140, 142, 144, 146 of side plates 24, 26, 124, 126 being a hole extending from inner surface 36 to outer surface 38, 138 (locating hole 140 extends from the inner surface to the outer surface of angle plates 212). The method can further include provide chamfer plate 34, 134 which includes a plurality of opposing ends 74 each of which includes at least one locating feature 76 formed as an outwardly facing projection 76, each outwardly facing projection 76 of chamfer plate 34, 134 connecting with a respective one of the plurality of locating features 40, 42, 44, 46, 140, 142, 144, 146 (in particular, locating feature 46, 146) of side plates 24, 26, 124, 126 (and angle plates 212). The plurality of saw slot plates 12, 14, 16, 18, 20, 22, 112, 118, 120, 122 includes first saw slot plate 12, 112, second saw slot plate 14, third saw slot plate 16, fourth saw slot plate 18, 118, fifth saw slot plate 20, 120, and sixth saw slot plate 22, 122. At least one slot 50, 52, 54, 56 includes first slot 52, second slot 54, third slot 56, and fourth slot 58, first saw slot plate 12, 112 and second saw slot plate 14 together forming first slot 52 which is configured for receiving bone saw blade 30 to make anterior cut 58 in bone 28 which is femur 28, third saw slot plate 16 and fourth saw slot plate 18, 118 together forming second slot 52 which is configured for receiving bone saw blade 30 to make posterior cut 52 in femur 28, fifth saw slot plate 20, 120 and chamfer plate 34, 134 together forming third slot 54 which is configured for receiving bone saw blade 30 to make anterior chamfer cut 62 in femur 28, sixth saw slot plate 22, 122 and chamfer plate 34, 134 together forming fourth slot 56 which is configured for receiving bone saw blade 30 to make posterior chamfer cut 64 in femur 28. Inner surface 36 can be substantially parallel to outer surface 38, 138 of a respectively same side plate 24, 26, 124, 126. Each of side plates 24, 26, 124, 126 can be substantially identical to one another. Each of the plurality of saw slot plates 12, 14, 16, 18, 20, 22, 118, 120, 122 can be substantially identical to one another.

Each of side plates 24, 26 can be a first size or a second size. Each of the plurality of saw slot plates 12, 14, 16, 18, 20, 22 can be a first size or a second size. Side plates 24, 26 of both the first size and the second size and the plurality of saw slot plates 12, 14, 16, 18, 20, 22 of both the first size and the second size are connectable with each other. That is, side plates 24, 26 can be combined with saw slot plates 12, 14, 16, 18, 20, 22 and chamfer plate 34 of different sizes. In other words, saw slot plates 12, 14, 16, 18, 20, 22 and chamfer plate 34 of one size can be combined with side plates 24, 26 of various sizes (side plates 24, 26 would be substantially identical to one another). Similarly, side plates 24, 26 of one size can be combined with saw slot plates 12, 14, 16, 18, 20, 22 and chamfer plate 34 of various sizes.

Each of the plurality of saw slot plates 12, 14, 16, 18, 20, and 22, side plates 24, 26, and chamfer plate 34 can be formed discretely from one another and then connected to one another. That is, as described above, each of saw slot plates 12, 14, 16, 18, 20, and 22, side plates 24, 26, and chamfer plate can be formed as individual pieces which are detached from one another (such as by stamping). These individual pieces can then be assembled together and thereby respectively attached to one another to form cut block 10, for example.

The method can alternatively provide that the step of forming includes forming a base plate 111 which is connected to side plates 124, 126, the method further including folding each of side plates 124, 126 relative to base plate 111 along a plurality of fold lines 206. This is described above relative to FIG. 6.

The present invention further provides another method of forming bone cutting block 10. The method includes the steps of: stamping a plurality of walls 12, 14, 16, 18, 20, 22, 24, 26, 34, 112, 118, 120, 122, 134 from at least one blank; connecting, after the step of stamping, the plurality of walls together 12, 14, 16, 18, 20, 22, 24, 26, 34, 112, 118, 120, 122, 134, the plurality of walls 12, 14, 16, 18, 20, 22, 24, 26, 34, 112, 118, 120, 122, 134 defining at least one slot 50, 52, 54, 56 therebetween which is configured for receiving bone saw blade 30 therethrough to make a predefined cut in bone 28. The plurality of walls 12, 14, 16, 18, 20, 22, 24, 26, 34, 112, 118, 120, 122, 134 includes a plurality of saw slot plates 12, 14, 16, 18, 20, 22, 112, 118, 120, 122 and two side plates 24, 26, 124, 126. The method further includes supporting the plurality of saw slot plates 12, 14, 16, 18, 20, 22, 112, 118, 120, 122 using side plates 24, 26, 124, 126 the plurality of saw slot plates 12, 14, 16, 18, 20, 22, 112, 118, 120, 122 each including a plurality of ends 68 opposing one another, each of the plurality of ends 68 including a locating feature 70, 170, each of side plates 24, 26, 124, 126 including a plurality of locating features 40, 42, 44, 46, 140, 142, 144, 146 (angle plates 212 include locating hole 140). Each locating feature 70, 170 of the plurality of saw slot plates 12, 14, 16, 18, 20, 22, 112, 118, 120, 122 is connected with a respective one of the plurality of locating features 40, 42, 44, 140, 142, 144 of side plates 24, 26 (locating hole 140 extends from the inner surface to the outer surface of angle plates 212) and side plates 24, 26, 124, 126 thereby opposing one another. Saw slot plates 12, 14, 16, 18, 20, 22, 112, 118, 120, 122 defining at least one slot 50, 52, 54, 56 therebetween which is configured for receiving bone saw blade 30, each locating feature 70, 170 of the plurality of saw slot plates 12, 14, 16, 18, 20, 22, 112, 118, 120, 122 being an outwardly facing projection 70, 170, each side plate 24, 26, 124, 126 including inner surface 36 and opposing outer surface 38, 138, inner surface 36 facing the plurality of saw slot plates 12, 14, 16, 18, 20, 22, 112, 118, 120, 122, each of the plurality of locating features 40, 42, 44, 46 of side plates 24, 26, 124, 126 (and angle plates 212) being a hole extending from inner surface 36 to outer surface 38, 138 (and, relative to locating features 140, the inner surface and outer surface of angle plates 212). The method further includes providing a chamfer plate 34, 134 which includes a plurality of opposing ends 74 each of which includes at least one locating feature 76 formed as an outwardly facing projection 76, each outwardly facing projection 76 of chamfer plate 34, 134 connecting with a respective one of the plurality of locating features 40, 42, 44, 46, 140, 142, 144, 146 (in particular, locating feature 46, 146) of side plates 24, 26, 124, 126. The plurality of saw slot plates 12, 14, 16, 18, 20, 22, 112, 118, 120, 122 includes first saw slot plate 12, 112, second saw slot plate 14, third saw slot plate 16, fourth saw slot plate 18, 118, fifth saw slot plate 20, 120, and sixth saw slot plate 22, 122. At least one slot 50, 52, 54, 56 includes first slot 52, second slot 54, third slot 56, and fourth slot 58. First saw slot plate 12, 112 and second saw slot plate 14 together form first slot 52 which is configured for receiving bone saw blade 30 to make anterior cut 58 in bone 28 which is femur 28. Third saw slot plate 16 and fourth saw slot plate 18, 118 together form second slot 52 which is configured for receiving bone saw blade 30 to make posterior cut 52 in femur 28. Fifth saw slot plate 20, 120 and chamfer plate 34, 134 together form third slot 54 which is configured for receiving bone saw blade 30 to make anterior chamfer cut 62 in femur 28. Sixth saw slot plate 22, 122 and chamfer plate 34, 134 together form fourth slot 56 which is configured for receiving bone saw blade 30 to make posterior chamfer cut 64 in femur 28. Inner surface 36 can be substantially parallel to outer surface 38, 138 of a respectively same side plate 24, 26, 124, 126. Each of side plates 24, 26, 124, 126 can be substantially identical to one another. Each of the plurality of saw slot plates 12, 14, 16, 18, 20, 22, 118, 120, 122 is substantially identical to one another. Each of the side plates 24, 26 can be a first size or a second size. Each of the plurality of saw slot plates 12, 14, 16, 18, 20, 22 can be a first size or a second size. Side plates 24, 26 of both the first size and the second size and the plurality of saw slot plates 12, 14, 16, 18, 20, 22 of both the first size and the second size are connectable with each other. Each of the plurality of saw slot plates 12, 14, 16, 18, 20, 22, side plates 24, 26, and chamfer plate 34 can be formed discretely from one another and then connected to one another. The method can alternatively provide that the step of forming includes forming a base plate 111 which is connected to side plates 124, 126, the method further including folding each of the side plates 124, 126 relative to base plate 111 along a plurality of fold lines 206.

According to an alternative embodiment of the present invention, the top-most and bottom-most locating (boss) holes in the side plates of the cutting block are open along one side in which to receive the corresponding bosses from the corresponding saw slot plates. These locating holes correspond respectively to the outermost saw slot plates for forming the anterior cut slot and the posterior cut slot. Thus, the top-most hole can be open towards the longitudinal end, and the bottom-most hole can be open towards the other longitudinal end.

According to another embodiment of the present invention, the cutting block of FIG. 1, for example, can have inserts (which can also be referred to as ends), one insert attached to the exterior side (that is, the outer surface) of each side plate. The inserts can be made of metal or plastic and can be formed by way of machining, molding. The insert could be aluminum that is anodized for color purposes or plastic for color and appearance. If the insert is plastic, the insert can optionally be made of a hard plastic such as Radel (i.e., RadelR) and may or may not have an additive such as glass filler (the Radel plastic can be polyphenylsulfone). The inserts serve, for example, to cover the welds associated with attaching the bosses of the saw slot plates and the chamfer plate to the side plates and to cover any non-level portions on the exterior sides of the side plates (i.e., due to protrusions from the bosses extending to the exterior side of the side plates). For instance, when the side plates are welded (such as by laser welding) to the interior plates (the saw slot plates and the chamfer plate), a filler can be used to even out the exterior surface (that is, the outer surface) of the side plate and the weld can be polished, the filler being used so that no seams or cracks are in the weld areas (such seams or cracks could be disadvantageous and could prevent proper sterilization of the cutting block if the cutting block is to be reusable). The inserts can add color to the cutting block and/or be etched so as to distinguish vendor and size relative to the cutting block. The inserts can be mechanically attached to the cutting block by way of a boss, a pad (i.e., a structure which can snap into a slot or form a dovetail fit with the side plate), staking, and/or press fit interference. The inserts can be attached to the respective side plate using an interference fit, for example; for instance, the inserts can each have one or more tabs/bosses which form an interference fit with one or more corresponding holes in the side plate. The inserts can be used with any other embodiment of the cutting block disclosed herein, such as the embodiment shown in FIG. 1. Further, the insert can have a through-hole extending which aligns with the pin hole (such as pin hole 48) of a respective side plate so that a pin (such as pin 32) can extend through both the insert and a respective side plate and thereby attach and/or align the cutting block to the femur.

According to another embodiment of the present invention, the cutting block can have a face plate. The face plate can be as shown in FIG. 6 or can be a separate piece which is attached to the side plates and/or the saw slot plates and/or the chamfer plate on the front side of the cutting block (the side facing the surgeon). The thickness of the face plate is only a fraction of the width of the side plate. The face plate can be removable from the remainder of the cutting block or can be permanently attached to the remainder of the cutting block. The face plate can be snap-fit to the cutting block, such as if the face plate is made of plastic. If the fit is permanent, then the face plate is assembled to the cutting block only one time and the connection would have to be broken to remove the face plate. If the face plate is made of metal, the face plate can be snapped with tabs to corresponding features (such as holes) of the cutting block. Alternatively, the metal face plate could be welded (for example, to close up any seams, cracks, or cavities for purposes of sterilization) to the cutting block and thereby be reusable. Alternatively, the metal face plate could be staked to the cutting block and optionally be disposable. If the face plate is made of metal, the metal can be made of, for example, stainless steel, such as a medical grade stainless steel. The metal face plate can be formed by stamping, for example. A plastic face plate can be, for example, made of a hard plastic, which can be for example Radel (i.e., RadelR) and may or may not have an additive, such as a glass filler. The plastic face plate can be, for example, formed by injection molding, extrusion, or machining. The face plate can further include centrally-located pin holes which can align with holes in the side plate or holes adjacent or near the side plates, these pin holes being used to receive an alignment pin or screw, as described above. The connection between the face plate and the side plates can be such that the face plate includes at least one protrusion for mating with a slot on a side plate to thereby connect the face plate to the side plate. Each lateral side (the sides adjacent the side plates) can include at least one such protrusion, and each side plate along one longitudinal side thereof can include a corresponding number of slots to receive the protrusions (for example, one slot per protrusion). For instance, each side of the face plate can include two protrusions arranged vertically to one another, one protrusion being positioned above a centrally-located pin hole, the other protrusion being positioned below the centrally-located pin hole. The protrusion can be a dovetail features. The slot (which can also be called a depression) for accepts the protrusion can be a female dovetail. The protrusion of the face plate can be welded, staked, or snap-fit to the side plate by way of the depression. For instance, the depression accepting the protrusion can form a clearance with the protrusion, the protrusion sliding frontally or from the side (laterally) into the depression; after so sliding into the depression, the protrusion can be welded or staked to the depression. For a snap-fit arrangement, the protrusion can form an interference fit with the depression, and the protrusion can be pushed into the depression. Further, the side plates each include relief slots along one longitudinal side (from the edge) of the slide plate. For instance, four such reliefs can be positioned along the rear edge (the side facing the femur) of each side plate and can be aligned with the corresponding anterior slot, posterior slot, anterior chamfer slot, and posterior chamfer slot. Each relief serves to allow the saw blade to swing out farther within the respective saw blade slot relative to the side plates. Optionally, depending upon the design of the reliefs, the reliefs could be used to slide the respective saw slot plate into a respective slot. The face plate can omit or can include one or more windows so that the surgeon can see the femur; such windows can be located in the anterior side and/or the posterior region of the face plate.

According to another embodiment of the present invention, the bottom saw slot plate (i.e., saw slot plate 16), the bottom two saw slot plates (i.e., saw slot plates 16 and 18), or any other of the saw slot plates or chamfer plate can be removable; that can be accomplished at least in part by not enclosing and/or not welding the ends of the saw slot plates (or chamfer plate) that are desired to be removable. Further, as in FIG. 6, the cutting block can include angled side plates near the top of the side plates, these angled side plates angled inwardly. Further, the initial pinning holes can be the isolated single holes at the front of the cutting block, these single holes being centrally located as shown in FIG. 6. Further, the cutting block can include four pinning blocks which provide holes which serve as pin guides; such pinning blocks can be attached, for example, to the inner surface of the side plates at the top left, top right, bottom left, and bottom right of the cutting block, each pinning block including three pin holes (while not clearly shown in FIG. 6, such pinning blocks can be used in FIG. 6). By way of the pin holes, pins can be guided all the way through the cutting block. The centrally located pin holes (the stand-alone pin holes) can provide for initial pinning and location of the cutting block on the distal femur. Depending upon a surgeon's preferred method of use, two pins can be inserted in the top pinning blocks (one per block) prior to making one of the cuts (such as the anterior cut); then these two pins can be removed and two pins can be inserted in the bottom pinning blocks (one per block) prior to making another one of the cuts (such as the posterior cut). Whether to leave the initial pins in the stand-alone pin holes and what order and how many pins to insert relative to the pinning blocks is subject to the individual surgeon's preference. The face plate can include pin holes to align with and thereby match the pin holes formed by the remainder of the cutting block. Each of the pin holes, including the stand-alone pin holes, provide for inside pinning (pinning inside the cutting block). Alternatively, the centrally located, stand-alone pin holes can be positioned to the outside of the side plates and thereby provide for outside pinning, and the face plate can be designed to match the positioning of these pin holes. As in FIG. 6, the face plate can include a centrally located, transversely extending window, the window including slants to accommodate the saw angle for the chamfer cuts. The face plate can, optionally, include another window for the anterior cut and another window for the posterior cut. Further, the face plate, as shown in FIG. 6, can have two additional windows—at top window and a bottom window—so that the surgeon can look through the cutting block and the face plate to see the femur. This cutting block (all but the face plate)

can be made of all metal, for example, and the face plate can be made of metal and/or plastic.

According to another embodiment of the present invention, the cutting block can have side plates that are stepped inwardly running from the posterior portion to the anterior portion of the cutting block (or vice versa). The step can be a sharp ninety-degree angle extending between the posterior portion and the anterior portion of the side plate or can have an angled transition. While the cutting block of the present invention can omit position tabs or position holes for a positioning/alignment pin, the side plates can each have a position tab extending from the outside of the side plates. These position tabs can be formed by stamping, forming a relief, and bending the tab out of the side of the side plate. These position tabs are used to receive an alignment pin. Such a cutting block can serve as minimally invasive styled cutting block. Pinning blocks can be at the anterior portion (or the posterior portion) of the cutting block, one on each side adjacent the side plates. The pinning blocks can each be formed from a cylindrical metallic piece, such as a metal rod with holes formed therein, and three such pinning holes, for example, can be formed therein can be positioned in a triangular configuration. This cutting block can also have a face plate, the face plate including anterior, posterior, and chamfer cutting slots (as in FIG. 6) and pinning holes that correspond to the pinning blocks. The face plate can be translucent. The face plate can also be stepped to match the contour of the remainder of the cutting block (i.e., the contour formed by the stepped configuration of the side plates). Alternatively, angle plates can be used at the top of the side plates, the angle plates being angled inwardly to accommodate a minimally invasive surgical procedure. The angle plates can be attached to the anterior side edge of the side plates or can be attached to the face plate; under either scenario, the angle plates can be folded along fold lines to form the box-like shape of the cutting block. Further, rather than having a step, the side plates can each have an angle plate that angles inwardly to the anterior edge of the cutting block.

According to another embodiment of the present invention, a two-piece cutting block can be provided according to the present invention. For example, one piece of this cutting block can be the plate shown in FIG. 6, this plate including the base plate, the side plates, the angle plates, and the outer-most saw slot plates attached to the base plate as shown in FIG. 6. These pieces can be folded relative to one another. The first plate can be folded to form a shell (including the base plate, side plates, and angle plates). The second piece can be another plate that is stamped, for example, and is attached generally to the rear (toward the femur) of the base plate. Towards the anterior end of this plate, this plate can be folded toward the base plate and form a bottom planar surface for the anterior cut slot. Near the center of this plate, the plate can be bent inward toward the base plate to form a surface acting in concert with the upwardly projecting slant of the base plate, these two surfaces forming an anterior chamfer cut sliding surface. Further, this same bend can form another planar surface that cooperates with the downwardly projecting slant of the base plate, these two surfaces forming a posterior chamfer cut sliding surface. Further, the bottom (posterior) end of this second plate can be bent inwardly toward the base plate to form the a top planar surface for the posterior cut slot; alternatively, if a posterior cut slot is not desired for this cutting block, then the posterior end of this second plate can be attached (i.e., by welding) to the saw slot plate forming the bottom of the cutting block. This second plate can be attached to the side plates by way of welding. Further, in the central bend for the chamfer cuts, this second plate can have pin holes formed therein near the lateral edges (near the side plates) of this second plate, these pin holes cooperating with centrally-located pin holes of the base plate. Thus, both plates can be stamped and/or machined, the holes therein also being stamped, machined, and/or drilled. Each plate can be created in the flat (from one or more blanks, such as a metal blank), the blank being punched out to form the plates, the plates then being folded. The two plates (the two pieces) can be laser welded together at their edges and filled.

Various supports or accessory components (combination or materials) can be added to any layout, pinning hole options, a front face plate, or a rear face plate and thereby further customize the cutting block of the present invention. For instance, the cutting block made out of metal can have a metallic or plastic face plate (as discussed above). Further, a front and/or rear face plate can be added to the cutting block. While not shown in the drawings, the rear face plate (the rear of the cutting block being that portion which abuts the transverse surface of the distal end of the femur) can be metallic or plastic and can be similar to the front face plate as discussed above. Having both a front and rear face plate would form more of an enclosure about the metallic cutting block. The face plates (the front and/or rear face plates) provide a cover for the components of the cutting block and provide a solid straight sheet on these faces. Further customization can include removal of the posterior portion of the cutting block (or any other portion, such as the anterior portion, as desired and that permits the cutting block to still be functional), the removal posterior portion optionally being the saw slot plates forming the slot for the posterior cut. The layout refers to the design of the cutting block, such as the orientation of the pinning holes, the distance between the saw slot plates, and the angle provided by the saw slot plates forming the slot for the anterior cut, and the angle provided by the saw slot plates forming the slot for the posterior cut, for example. Further, various attachments (such as vendor attachments) can be attached to the cutting block of the present invention. For example, attachments can include such devices as alignment guides, alignment rods (which can include carbon), an alignment guide using the intramedullary canal, and/or a tibia alignment guide, for example. The cutting block of the present invention can include notches to accommodate the mounting of various attachments used on the cutting block.

Each of the embodiments described herein can be used by a surgeon in a similar manner. That is, the cutting block can be placed against the transverse surface of the distal end of the femur, the transverse surface being formed by a transverse cut through the femur. Further, upon pinning or otherwise aligning the cutting block against the femur, the four cuts (anterior, posterior, anterior chamfer, and posterior chamfer cuts) can be made into the femur (less cuts can be made if so desired by the surgeon or if the cutting block omits a cutting slot).

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A bone cutting block, comprising:
a plurality of saw slot plates each including a pair of opposite end portions, each end portion of said pair including a locating feature; and
two side plates opposing one another, including a plurality of locating features, and supporting said plurality of saw slot plates, said plurality of supported saw slot plates defining at least one slot therebetween which is configured for receiving a bone saw blade therethrough to make a predefined cut in a bone, each said locating feature of said plurality of saw slot plates forming an interference fit with a respective one of said plurality of locating features of said side plates.

2. The bone cutting block of claim 1, wherein each said locating feature of said plurality of saw slot plates is an outwardly facing projection, each said side plate including an inner surface and an opposing outer surface, said inner surface facing said plurality of saw slot plates, each of said plurality of locating features of said side plates being a hole extending from said inner surface to said outer surface.

3. The bone cutting block of claim 2, further including a chamfer plate which includes a plurality of opposing ends each of which includes at least one locating feature formed as an outwardly facing projection, each said outwardly facing projection of said chamfer plate connecting with a respective one of said plurality of locating features of said side plates.

4. The bone cutting block of claim 3, further including a base plate which is connected to said side plates by way of a plurality of folds.

5. A bone cutting block, comprising:
a plurality of saw slot plates each including a pair of opposite end portions, each end portion of said pair including a locating feature;
two side plates opposing one another, including a plurality of locating features, and supporting said plurality of saw slot plates, said plurality of supported saw slot plates defining at least one slot therebetween which is configured for receiving a bone saw blade therethrough to make a predefined cut in a bone, each said locating feature of said plurality of saw slot plates forming an interference fit with a respective one of said plurality of locating features of said side plates, wherein each said locating feature of said plurality of saw slot plates is an outwardly facing projection, each said side plate including an inner surface and an opposing outer surface, said inner surface facing said plurality of saw slot plates, each of said plurality of locating features of said side plates being a hole extending from said inner surface to said outer surface; and
a chamfer plate which includes a plurality of opposing ends each of which includes at least one locating feature formed as an outwardly facing projection, each said outwardly facing projection of said chamfer plate connecting with a respective one of said plurality of locating features of said side plates, wherein said plurality of saw slot plates includes a first saw slot plate, a second saw slot plate, a third saw slot plate, a fourth saw slot plate, a fifth saw slot plate, and a sixth saw slot plate, said at least one slot including a first slot, a second slot, a third slot, and a fourth slot, said first saw slot plate and said second saw slot plate together forming said first slot which is configured for receiving a bone saw blade to make an anterior cut in a bone which is a femur, said third saw slot plate and said fourth saw slot plate together forming said second slot which is configured for receiving a bone saw blade to make a posterior cut in a femur, said fifth saw slot plate and said chamfer plate together forming said third slot which is configured for receiving a bone saw blade to make an anterior chamfer cut in a femur, said sixth saw slot plate and said chamfer plate together forming said fourth slot which is configured for receiving a bone saw blade to make a posterior chamfer cut in a femur, said inner surface being substantially parallel to said outer surface of a respectively same said side plate.

* * * * *